United States Patent

Rhomberg et al.

[11] 3,988,460
[45] Oct. 26, 1976

[54] CYCLOPENTENOQUINOLONE COMPOUNDS FOR TREATING BACTERIAL INFECTIONS

[75] Inventors: Alfred Rhomberg, Mannheim-Neuostheim, Germany; Herbert Berger, Mannheim-Kafertal, Germany; Kurt Stach, deceased, late of Mannheim-Waldhof, Germany; by Werner Plattner, executor, Austria; Wolfgang Vomel, Mannheim, Germany; Winfriede Sauer, Mannheim-Wallstadt, Germany

[73] Assignee: Boehringer Mannheim G.m.b.H., Mannheim, Germany

[22] Filed: Mar. 13, 1975

[21] Appl. No.: 558,101

Related U.S. Application Data

[62] Division of Ser. No. 349,898, April 10, 1973, Pat. No. 3,901,895.

[30] Foreign Application Priority Data
May 10, 1972 Germany.......................... 2222833

[52] U.S. Cl. ............................................. 424/258
[51] Int. Cl.² .......................................... A61K 31/47
[58] Field of Search ................................... 424/258

[56] References Cited
UNITED STATES PATENTS
3,506,667  4/1970  Kaminsky...................... 260/287 R FOREIGN PATENTS OR APPLICATIONS
2,011,885  9/1971  Germany...................... 260/287 R Primary Examiner—Jerome D. Goldberg
Attorney, Agent, or Firm—Burgess, Dinklage & Sprung

[57] ABSTRACT

Certain novel cyclopentenoquinolone derivatives of the formula:

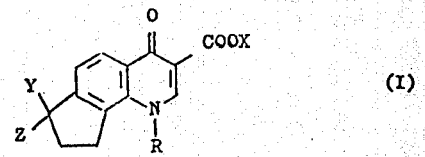

wherein
R and X, which may be the same or different, are hydrogen or lower saturated or unsaturated aliphatic hydrocarbyl;
Y is hydroxyl or lower alkoxy or lower acyloxy (i.e., alkanoyloxy); and
Z is hydrogen or lower alkoxy, or, together with Y, represents an oxo or lower alkenyldioxy radical; and the pharmacologically compatibile salts thereof
are outstandingly effective as anti-microbials, particularly for applications against infections of the urinary tract.

20 Claims, No Drawings

CYCLOPENTENOQUINOLONE COMPOUNDS FOR TREATING BACTERIAL INFECTIONS

This application is a divisional of Ser. No. 349,898, filed on Apr. 10, 1973 and issued to U.S. Pat. No. 3,901,895 on Aug. 26, 1975.

The present invention is concerned with new cyclopentenoquinolone compounds and with therapeutic compositions and uses of such compounds.

The new cyclopentenoquinolone derivatives according to the present invention are compounds of the formula:

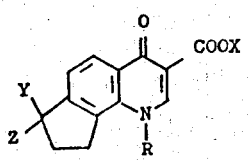

wherein
R and X, which may be the same or different, are hydrogen or lower saturated or unsaturated aliphatic hydrocarbyl; Y is hydroxyl or lower alkoxy or lower acyloxy (i.e., alkanoyloxy); and
Z is hydrogen or lower alkoxy, or, together with Y, represents an oxo or lower alkenyldioxy radical, and the pharmacologically compatible salts thereof.

The new compounds (I) according to the present invention differ from structurally similar compounds, such as those described in German Patent Specification No. 1,770,951, by being substituted in the cyclopentene ring.

Surprisingly, the new compounds possess, in comparison with the known compounds, about the same antimicrobial activity in vitro but a substantially stronger in vivo action, especially in the urinary tract.

The new compounds (I) according to the present invention can be prepared, for example, by cyclizing compounds of the general formula:

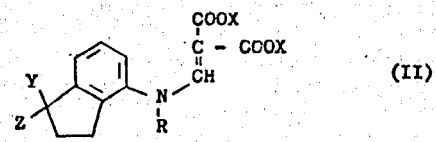

wherein X, Y, Z and R have the same meanings as above, whereafter, if desired, the product obtained is N-alkylated, N-alkenylated or N-alkynylated and/or subsequently, if desired, rearranged, hydrolyzed, esterified, ketalized, reduced, oxidized, etherified, acylated and/or converted into pharmacologically compatible salts.

The cyclization is preferably carried out under the conditions of the Gould-Jacobs reaction in an inert solvent, for example, in diphenyl ether, diethyl phthalate or in a mineral oil, at a temperature of 200°–280° C, preferably at about 250° C. However, it is also possible to carry out the cyclization by means of agents splitting off water or alcohol, for example, concentrated sulfuric acid, polyphosphoric acid or phosphorus oxychloride.

The N-alkylation, N-alkenylation or N-alkynylation can be carried out, for example, with alkyl, alkenyl or alkynyl halides or sulfuric acid esters or sulfonic acid esters, in the presence of acid-binding agents, for example, potassium carbonate, sodium hydroxide or the like, preferably in an inert solvent.

When R in the compound obtained is an unsaturated aliphatic hydrocarbon radical, if desired, a rearrangement of the double bond can subsequently be carried out with a base. Thus, for example, the reararrangement of N-allyl-quinolones is preferably carried out with an aqueous alkali, such as an aqueous solution of sodium hydroxide, or also with alcoholates or strong organic bases, possibly with the addition of solubilizing agents, for example alcohols, glycols, cyclic ethers or dimethyl sulfoxide. If the N-allyl-quinolones are prepared from quinolones (R=H) and allyl halides or allyl esters of strong acids, with the addition of an acid-binding agent (weak alkali), then, after the addition of a strong base and subsequent boiling, the rearrangement can be carried out directly in the same reaction vessel, without intermediate isolation of the allyl-quinolones.

Esters of general formula (I) can, if desired, be subsequently converted into the corresponding carboxylic acids by saponification and carboxylic acids can be esterified. Saponification can be carried out with dilute alkalis or, preferably, with dilute acids at an elevated temperature. Esterification can be carried out by boiling the free acid in an appropriate alcohol, with the addition of a catalytic amount of a strong acid, or, especially mildly, by reaction with an appropriate diazoalkane.

An ether group in the 7-position can be split off hydrolytically, for example, by boiling in concentrated hydrobromic acid. Conversion of a 7-oxo group into a ketal can be carried out by reaction with an ortho ester or a lower alcohol, or, preferably, with a glycol, cyclic ketals thereby being obtained, in the presence of an acidic catalyst, for example, hydrogen chloride or a cation exchanger in acid form.

Reduction of the 7-oxo group can be carried out, for example, with a complex hydride, such as sodium borohydride, or by catalytic hydrogenation with Raney nickel or a noble metal catalyst, in an inert solvent. As solvent, there can be used, for example, an aqueous alkali, dimethyl formamide or glacial acetic acid.

The 7-hydroxy compounds thus obtained can subsequently by acylated by reaction with an active acid derivative, for example, an anhydride, acid chloride or acid imidazolide. If desired, the 7-hydroxy compounds can be etherified with conventional alkylation agents.

A 7-hydroxy group can also be oxidized to an oxo group, for example, with hydrogen peroxide in aqueous alkali or with ferric chloride, potassium permanganate, chromic anhydride or lead tetraacetate in glacial acetic acid or in a mixture of glacial acetic acid and sulfuric acid.

The starting materials of general formula (II) can be obtained, for example, from the appropriate 4-aminoindan-1-ones or N-lower alkylated derivatives thereof, which are known from the literature, by reaction with ethoxymethylenemalonic esters.

The following Examples are illustrative of the preparation of compounds of the present invention:

EXAMPLE 1

Preparation of
1-Ethyl-3-carboxy-1,4-dihydro-7-hydroxy-cyclopentene-[1,2-h]quinol-4-one.

0.11 g 3-carboxy-4,7-dihydroxy-cyclopenteno[1,2-h]-quinoline, 0.32 g potassium carbonate, 0.35 g ethyl iodide and 4.5 ml dimethyl formamide were stirred for 45 minutes at 70° C. A further 0.1 g ethyl iodide was then added and, after 45 minutes, yet another 0.15 g ethyl iodide were added and stirring thereafter continued for 30 minutes, the temperature being maintained at 70° C during the whole of the reaction period. Subsequently, inorganic material was filtered off with suction and the filtrate was evaporated to dryness. The residue was taken up in 0.5 ml water, 1 ml 2N aqueous sodium hydroxide solution was added and the reaction mixture boiled for 5 minutes. After cooling, the reaction mixture was acidified with 2N hydrochloric acid. Almost pure 1-ethyl-3-carboxy-1,4-dihydro-7-hydroxycyclopenteno[1,2-h]quinol-4-one thereby precipitated out and was filtered off and washed with a little alcohol. The yield was 0.05 g. After recrystallization from dimethyl formamide, the compound has a decomposition point of 269°–275° C.

In an analogous manner, 1-n-propyl-3-carboxy-1,4-dihydro-7-hydroxy-cyclopenteno[1,2-h]quinol-4-one can be obtained when using n-propyl instead of ethyl iodide.

The 3-carboxy-4,7-dihydroxy-cyclopenteno[1.2-h]-quinoline used as starting material was obtained in the following manner:

1.66 g 4-amino-indan-1-one, 4 ml toluene and 2.67 g ethoxymethylene-malonic ester were heated under reflux for two hours, subsequently evaporated to dryness in a vacuum and the evaporation residue triturated with a little ether. There was obtained 1.4 g of crude product which was taken up in a little carbon tetrachloride. The hot solution was mixed with active charcoal, the charcoal was then filtered off and the filtrate was evaporated to dryness. There was obtained 1 g 4-(2,2-bisethoxycarbonyl-vinylamino)-1-indanone, which has a melting point of 124°–128° C.

2.4 g 4-(2,2-bis-ethoxycarbonyl-vinylamino)-1-indanone were heated for ten minuttes at 250° C in 48 ml diphenyl ether. After cooling, the reaction mixture was diluted with a mixture of ether and ligroin (1:1) and the 3-ethoxycarbonyl-4-hydroxy-[1,2-h]cyclopenten-7-one quinoline which thereby precipitated out was filtered off with suction. The yield was 1.3 g and this compound has a decomposition point of about 310° c.

100 mg 3-ethoxycarbonyl-4-hydroxy[1,2-h]cyclopenten-7-quinoline were boiled for 75 minutes in 1.5 ml concentrated hydrochloric acid, subsequently diluted with water and the preciptiated 3-carboxy-4-hydroxy[1,2-h]-cyclopenten-7-one-quinoline filtered off and dried. The yield was 70 mg. After purification by recrystallization from dimethyl formamide, the compound has a decomposition point of >300° C.

450 mg 3-carboxy-4-hydroxy[1,2-h]cyclopenten-7-one-quinoline were suspended in 13.5 ml methanol and 4.5 ml 2N aqueous sodium hydroxide solution added thereto. 420 mg sodium borohydride were then added thereto, within the course of ten minutes. The temperatures hereby increased to about 35°–45° C. The reaction mixture was stirred for a further 30 minutes at this temperature, mixed with active charcoal and filtered. The filtrate was evaporated until the greater part of the methanol was removed. By the addition of water, a clear solution was obtained. This was then acidified with 2N hydrochloric acid. Pure 3-carboxy-4,7-dihydroxy-cyclopenteno[1,2-h]quinoline thereby precipitated out and was filtered off with suction, washed with a little water and dried. The yield was 220 mg and the product has a decomposition point of 272°–279° C.

EXAMPLE 2

Preparation of
1-Ethyl-3-methoxycarbonyl-1,4-dihydro-7-hydroxy-cyclopenteno[1,2-h]quinol-4one.

0.54 g 1-ethyl-3-carboxy-1,4-dihydro-7-hydroxycyclopenteno[1,2-h]quinol-4-one, 1.3 g potassium carbonate, 1.4 g methyl iodide and 5 ml dimethyl formamide were stirred for 90 minuts at 50° C. Subsequently, inorganic material was filtered off with suction and the filtrate mixed with a mixture of ether and ligroin (1:1). Almost pure 1-ethyl-3-methoxycarbonyl-1,4-dihydro-7-hydroxy-cyclopenteno[1,2-h]quinol-4-one thereby precipitated out. The yield was 0.3 g and the product has a melting point of 190° C.

EXAMPLE 3

Preparation of
1-Ethyl-3-carboxy-1,4-dihydro-7-hydroxy-cyclopenteno-[1,2-h]quinol-4one.

0.5 g 1-ethyl-3-methoxycarbonyl-1,4-dihydro-7-hydroxycyclopenteno[1,2-h]quinol-4-one were boiled for 10 minutes in 3 ml 2N aqueous sodium hydroxide solution. Subsequently, the reaction mixture was acidified with 2N hydrochloric acid and the 1-ethyl-3-carboxy-1,4-dihydro-7-hydroxy-cyclopenteno[1,2-h]quinol-4-one which precipitated out was filtered off and dried. The yield was 0.4 g. The product is identical with that of Example 1.

EXAMPLE 4

Preparation of
7-Acetoxy-3-ethoxycarbonyl-4-hydroxycyclopenteno-[1,2-h]quinoline 27.6 g 4-(2,2-bis-ethoxycarbonyl-vinylamino)-1-acetoxyindane were introduced in 270 ml diphenyl ether heated to 250°–260° C. This temperature was maintained for ten minutes and then the reaction mixture was rapidly cooled. 7-acetoxy-3-ethoxycarbonyl-4-hydroxy-cyclopenteno[1,2-h]quinoline was precipitated out by the addition of about 270 ml ligroin. After filtering off and drying, there were obtained 14.7 g of crude product which melts, with decomposition, at 230°–239° C. The product can be further worked up.

The 4-(2,2-bis-ethoxycarbonyl-vinylamino)-1-acetoxyindane used as starting material was prepared as follows:

27.5 g 4-nitroindan-1-one were dissolved in 410 ml dioxan and 252 ml methanol and hydrogenated with hydrogen in the presence of Raney nickel at 50° C to give 4-amino-indan-1-one. The compound was not isolated. The catalyst was filtered off, 11.7 g sodium borohydride were added to the filtrate at 50° C, within the course of ten minutes, the reaction mixture was thereafter stirred for twenty minutes at 50° C and the solution was evaporated and treated with 150 ml water. The oil which separated was extracted with chloroform and the extract was dried and evaporated. There were obtained 23 g 4-aminoindan-1-ol. The crude product was not purified but was heated with 33.3 g ethoxymethylene-malonic ester and 70 ml toluene for 1 hour at 80° C. After evaporation of the solvent, there were obtained 49.3 g crude 4-(2,2-bis-ethoxycarbonyl-vinylamino)-1-hydroxy-indane, which was not purified but was heated, as crude product, with 250 ml acetic anhydride for thirty minutes under reflux. The reaction solution was filtered over active charcoal and the filtrate was evaporated in a vacuum. In this way, there were obtained 55.7 g crude 4-(2,2-bis-ethoxycarbonyl-vinylamino)-1-acetoxyindane. This crude product, which has a decomposition point of 213°–235° C, was used for the cyclization reaction.

EXAMPLE 5

Preparation of 1-Ethyl-3-carboxy-1,4-dihydro-7-hydroxy-cyclopenteno[1,2-h]quinol-4-one.

16 g 7-acetoxy-3-ethoxycarbonyl-4-hydroxy-cyclopenteno[1,2-h]quinoline, 35.2 g potassium carbonate, 240 mg potassium iodide, 128 ml methyl ethyl ketone and 38 ml ethyl bromide were stirred for 4 hours at 85° C. Subsequently, inorganic material was filtered off with suction and the filtrate treated with 12 g active charcoal. After filtering off the active charcoal, the filtrate was evaporated to dryness and the evaporation residue was heated under reflux with 160 ml 2N aqueous sodium hydroxide solution and 80 ml ethanol for 15 minutes. The greater part of the ethanol was then evaporated off. The remainder was treated with about 8 g active charcoal and, after filtering off the charcoal, was acidified with concentrated hydrochloric acid. The mixture was left to stand for about 1 hour at 0° C and then filtered. There were obtained 5.4 g 1-ethyl-3-carboxy-1,4-dihydro-7-hydroxy-cyclopenteno[1,2-h]quinol-4-one. After recrystallization from a mixture of dimethyl formamide and dioxan, there were obtained 4 g of pure product which has a decomposition point of 270° C. From the aqueous hydrochloric acid mother liquors, there precipitated out, after standing for some time, almost pure 7-hydroxy-3-carboxy-4-hydroxy-cyclopenteno[1,2-h]quinoline, which melts, with decomposition, at 285°–295° C. The yield was 1.9 g.

EXAMPLE 6

Preparation of 1-Allyl-3-carboxy-1,4-dihydro-7-hydroxy-cyclopenteno[1,2-h]quinol-4-one 2.73 g 7-hydroxy-3-ethoxycarbonyl-4-hydroxy-cyclopenteno[1,2-h]quinoline, 0.7 g potassium carbonate, 0.1 g potassium iodide, 22 ml dimethyl formamide and 6.05 g allyl bromide were stirred for 4 hours at a bath temperature of 95° C. Subsequently, inorganic material was filtered off with suction, the filtrate was evaporated to dryness in a vacuum and the evaporation residue was boiled for 15 minutes with 27 ml 2N aqueous sodium hydroxide solution and 14 ml ethanol. The alcohol was thereafter evaporated off. The residue was then carefully acidified with concentrated hydrochloric acid and the precipitated crystals were filtered off with suction. There were obtained 2.2 g crude 1-allyl-3-carboxy-1,4-dihydro-7-hydroxycyclopenteno[1,2-h]quinol-4-one. After recrystallization from a mixture of dioxan and dimethyl formamide, the compound melts, with decomposition, at 235°–238° C.

EXAMPLE 7

Preparation of 1-Ethyl-7-acetoxy-3-carboxy-1,4-dihydro-cyclopenteno[1,2-h]quinol-4-one.

850 mg 1-ethyl-7-hydroxy-3-carboxy-1,4-dihydrocyclopenteno[1,2-h]quinol-4-one were heated under reflux for 1 hour in 12.7 ml acetic anhydride. After cooling, the precipitated crystals were filtered off with suction and recrystallized from dimethyl formamide. There were obtained 650 mg pure 1-ethyl-7-acetoxy-3-carboxy-1,4-dihydro-cyclopenteno[1,2-h]quinol-4-one, which has a melting point of 228°–231° C.

EXAMPLE 8

Preparation of 1-Ethyl-3-ethoxycarbonyl-1,4-dihydro-7-hydroxy-cyclopenteno[1,2-h]quinol-4-one.

1.09 g 1-ethyl-3-carboxy-1,4-dihydro-7-hydroxy-cyclopenteno[1,2-h]quinol-4-one, 1.1 g potassium carbonate, 11 ml dimethyl formamide and 1.87 g ethyl iodide were stirred for 2 hours at 80° C. The inorganic material was then filtered off with suction from the hot reaction mixture, the filtrate was evaporated in a vacuum and the evaporation residue was taken up in 15 ml water. The crystals which separated out after some time were filtered off (1 g) and recrystallized from ethanol. There was obtained 0.75 g 1-ethyl-3-ethoxycarbonyl-1,4-dihydro-7-hydroxycyclopenteno[1,2-h]quinol-4-one, which has a melting point of 196° C.

EXAMPLE 9

Preparation of 7-Hydroxy-3-ethoxycarbonyl-4-hydroxycyclopenteno[1,2-h]quinoline.

4 g 7-acetoxy-3-ethoxycarbonyl-4-hydroxy-cyclopenteno[1,2-h]quinoline were suspended in 30 ml methanol. A solution of 650 mg sodium in 20 ml methanol was added thereto at 50° C within the course of one hour. At the end of this addition, the reaction mixture was further stirred for 15 minutes at 50° C, insoluble material was then filtered off and the filtrate was diluted with 20 ml methanol and then carefully acidified with concentrated hydrochloric acid. The solution was treated with active charcoal and, after filtering off, the active charcoal was evaporated to dryness. The evaporation residue was taken up with 10 ml water and neutralized with an aqueous solution of sodium bicarbonate. Upon standing in the cold, almost pure 7-hydroxy-3-ethoxycarbonyl-4-hydroxy-cyclopenteno[1,2-h]quinoline precipitated out. The yield was 2 g and the compound melts, with decomposition at 250° C.

EXAMPLE 10

Preparation of 1-Ethyl-3-carboxy-1,4-dihydro-7-ethoxy-cyclopenteno[1,2-h]quinol-4-one 1.1 g 1-ethyl-3-carboxy-1,4-dihydro-7-hydroxy-cyclopenteno[1,2-h]quinol-4-one, 8 ml 10N aqueous sodium hydroxide solution and 6 ml dioxan were heated to 80° C. 5.5 ml diethyl sulfate were then added dropwise, while stirring within the course of 4 hours. At the end of the addition, stirring was continued at 80° C for thirty minutes and, after cooling, mixed with some water. The reaction was then acidified with hydrochloric acid and the precipitated 1-ethyl-3-carboxy-1,4-dihydro-7-ethoxy-cyclopenteno[1,2-h]quinol-4-one filtered off and recrystallized from dioxan. The yield was 0.9 g and the product has a melting point of 168°–171° C.

EXAMPLE 11

Preparation of 1-Ethyl-3-carboxy-1,4-dihydro[1,2-h]cyclopenten-7-one-quinol-4-one.

1.35 g 3-ethoxycarbonyl-4-hydroxy[1,2-h]cyclopenten-7-one-quinoline, 2.65 g sodium carbonate and 13.5 ml dimethyl formamide were stirred at 70° C and a mixture of 2 ml ethyl iodide and 1 ml dimethyl formamide introduced within the course of two hours. After completion of the addition, stirring was continued for 1 hour, water was added and the precipitated material (0.7 g) was filtered off. This material was boiled out three times with 10 ml amounts of dioxan and filtered off from insoluble material, which was unreacted starting material. The combined filtrates were evaporated the residue recrystallized from ethanol. There were obtained 70 mg pure 1-ethyl-3-carbethoxy-1,4-dihydro[1,2-h]-cyclopenten-7-one-quinol-4-one, which has a decomposition point of 225°–250° C. By heating this ester with a dilute aqueous solution of sodium hydroxide, there was obtained 1-ethyl-3-carboxy-1,4-dihydro[1,2-h]cyclopenten-7-one-quinol-4-one, which has a decomposition point of 280°–290° C.

The same 1-ethyl-3-carboxy-1,4-dihydro[1,2-h]cyclopenten-7-one-quinol-4-one can also be obtained when, for example, 273 mg 1-ethyl-3-carboxy-1,4-dihydro-7-hydroxy-cyclopenten[1,2-h]-quinol-4-one is heated to the boil with about 1000 mg chromic anhydride in 2.7 ml 2N aqueous hydroxide solution and the progress of the reaction followed chromatographically, possibly with the addition of further chromic anhydride. The 1-ethyl-3-carboxy-1,4-dihydro[1,2-h]cyclopenten-7-one-quinol-4-one is precipitated out with hydrochloric acid. The yield is 150 mg.

EXAMPLE 12

Preparation of 1-(Prop-1'-en-1'-yl)-3-carboxy-1,4-dihydro-7-hydroxy-cyclopenteno[1,2-h]quinol-4-one 2 g 1-allyl-3-carboxy-1,4-dihydro-7hydroxy-cyclopenteno[1,2-h]quinol-4-one, 20 ml 5N aqueous sodium hydroxide solution and 10 ml ethylene glycol were heated to 120° C for 30 minutes. The reaction mixture was subsequently diluted with 50–70 ml water and acidified with concentrated hydrochlorid acid. The 1-(prop-1'-en-1'-yl)-3-carboxy-1,4-dihydro-7-hydroxy-cyclopenteno[1,2-h]quinol-4-one which precipitated out was filtered off with suction. The yield was 1.8 g. After recrystallization from a mixture of dimethyl formamide and dioxan, the product has a melting point of 253°–255° C.

The present invention also provides pharmaceutical compositions containing at least one of the new compounds of general formula (I) and/or at least one pharmacologically compatible salt thereof, in admixture with a solid or liquid pharmaceutical diluent or carrier.

The bacteriostatic activity of the instant compounds was measured by determining the absolute bacteriostatic minimum concentration against a number of representative species (see Table 1) and by measuring the excretion of the test compounds in urine and the bacteriostatic effectiveness of the urine after oral administration to rats (see Table 2).

The results are set out in the following Tables.

TABLE 1

| | | Absolute Bacteriostatic Minimum Concentrations in µg/ml | | | |
|---|---|---|---|---|---|
| | | | BACTERIUM GROUP | | |
| Test Substance [Prep. Ex. No.] | | Escherichia coli (106) | Escherichia coli (108) | Proteus mirabilis (298) | Proteus vulgaris (206) |
| 1-Ethyl-3-carboxy-1,4-dihydro-7-hydroxy-cyclopenteno[1.2-h]-quinolone-(4) | [1] | 2 | 1 | 4 | 2 |
| 1-Allyl-3 carboxy-1,4-dihydro-7-hydroxy-cyclopenteno[1,2-h]-quinolone-(4) | [6] | 2 | 1 | 4 | 2 |
| 1-Ethyl-7-acetoxy-3-carboxy-1,4-dihydro-cyclopenteno[1,2-h]quinolone-(4) | [7] | 1 | 0.5 | 0.25 | 0.5 |
| 7-Hydroxy-3-ethoxycarbonyl-4-hydroxy-cyclopenteno[1,2-h]-quinoline | [9] | >128 | >128 | >128 | >128 |
| Nalidixic acid (Nogram-Winthrop) | | 1 | 1 | 4 | 2 |
| Furadantin (Nitrofurantoin-Norwich) | | 4 | 4 | 256 | 128 |

TABLE 2

BACTERIOSTATIC ACTIVITY OF THE URINE OF RATS FOLLOWING ORAL ADMINISTRATION

Bacteriostatic maximum dilution of urine against Escherichia coli (106) determined in 50 ml (75 ml) urine samples 22 hours after 20 mg test compound per kg body weight had been orally administered. 6 (9) rats were employed for each experiment and every value recorded in the Table represents the results of each experiment.

| Test Compound | Prep. Ex. No. | Max. Dilution |
|---|---|---|
| 1-Ethyl-3-carboxy-1,4-dihydro-7-hydroxy-cyclopenteno[1.2-h]-quinolone-(4) | [1] | 1:1040 1:1400 1:672 |
| 1-Allyl-3-carboxy-1,4-dihydro-7-hydroxy-cyclopenteno[1.2-h]quinolone-(4) | [6] | 1:1024 1:960 1:1488 |
| 1-Ethyl-7-acetoxy-3-carboxy-1,4- | | |

-continued

| Test Compound | Prep. Ex. No. | Max. Dilution |
| --- | --- | --- |
| dihydro-cyclopenteno[1.2-h]-quinolone-(4) | [7] | 1:1800 |
| 7-Hydroxy-3-ethoxycarbonyl-4-hydroxy-cyclopenteno[1.2-h]quinoline | [9] | 1:1400 |
| | | 1:1820 |
| Nalidixic*acid | | 1:234 |
| | | 1:280 |
| | | 1:270 |
| Furadantin** | | 1:54 |
| | | 1:30 |
| | | 1:41 |
| | | 1:19 |
| | | 1:40 |
| | | 1:21 |

*Nogram-Winthrop
**Nitrofurantoin-Norwich

The compounds of general formula (I) can be administered centrally and parenterally in solution, suspension or in solid form by admixture with a solid or liquid pharmaceutical diluent or carrier. They are preferably administered in the form of tablets or dragees with a content of active material of 100–500 mg per tablet or dragee. The tablets can thereby contain further solid carrier materials, for example, starch, lactose, methyl cellulose, talc, highly dispersed silicic acid, high molecular weight fatty acids, magnesium stearate, gelatine, solid high molecular weight polymers (for example polyethylene glycols) and, if desired, also flavoring and/or coloring agents.

Suspensions are preferably administered with a content of active materials of 20–100 mg/ml, using water as the suspension agent. For the stabilization of the suspensions, there can be added high molecular weight, water-soluble materials, for example, cellulose ethers or polyethylene oxide. Furthermore, there can also be added sweetening agents, flavoring agents, odiferous materials and/or coloring agents. For injection solutions, the compounds of general formula (I) are preferably used in aqueous solution in amounts from 10–100 mg/dosage. Such injection solutions preferably also contain conventional additives, for example, stabilization agents, solubilizing agents, buffers mannitol or sodium chloride in the amount necessary to produce an isotonic solution.

The active compounds of this invention will be administered to the afflicted subject according to methods known to the skilled artisan after being formulated as disclosed hereinabove or otherwise as also known in the art. Particularly in the application of the instant compounds to prevent or combat infections of the urinary tract, dosages of from 10 to 500 mg/kg of body weight may be desirably used, and these dosages are conveniently administered three times a day. However, different dosages may be appropriate in a given set of circumstances.

It will be understood that the foregoing specification and examples are illustrative but not limitative of the present invention inasmuch as other embodiments within the spirit and scope of the invention will suggest themselves to those skilled in the art.

What is claimed is:

1. Method for treating bacterial infection in a subject afflicted with said infection comprising administering to said subject a bacteriostatically effective amount of a cyclopentenoquinolone compound of the formula:

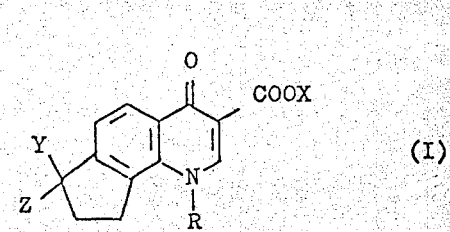

wherein
R is hydrogen, alkyl or alkenyl of up to six carbon atoms;
X is hydrogen, alkyl or alkenyl of up to six carbon atoms;
Y is hydroxyl, lower alkoxy or alkanoyloxy of up to six carbon atoms; and
Z is hydrogen or lower alkoxy of up to six carbon atoms; or
Z, together with Y, represents an oxo linkage; and the pharmacologically acceptable salts thereof.

2. Method as claimed in claim 1 wherein said compound is selected from the group consisting of
1-ethyl-3-carboxy-1,4-dihydro-7-hydroxycyclopenteno-[1,2-h]quinol-4-one;
1-Allyl-3-carboxy-1,4-dihydro-7-hydroxycyclopenteno-[1,2-h]quinol-4-one;
1-Ethyl-7-acetoxy-3-carboxy-1,4-dihydrocyclopenteno[1,2-h]quinol-4-one; and
7-Hydroxy-3-ethoxycarbonyl-4-hydroxy-cyclopenteno[1,2-h]quinoline.

3. Method as claimed in claim 1 wherein R in the formula is hydrogen.

4. Method as claimed in claim 1 wherein X in the formula is hydrogen.

5. Method as claimed in claim 1 wherein R in the formula is lower alkyl of from 1 to 6 carbon atoms.

6. Method as claimed in claim 1 wherein R in the formula is lower alkenyl of from 2 to 6 carbon atoms.

7. Method as claimed in claim 1 wherein X in the formula is lower alkyl of from 1 to 6 carbon atoms.

8. Method as claimed in claim 1 wherein X in the formula is lower alkenyl of from 2 to 6 carbon atoms.

9. Method as claimed in claim 1 wherein Y in the formula is hydroxyl.

10. Method as claimed in claim 1 wherein Y in the formula is lower alkoxy of from 1 to 6 carbon atoms.

11. Method as claimed in claim 1 wherein Y in the formula is lower alkanoyloxy of from 1 to 6 carbon atoms.

12. Method as claimed in claim 1 wherein Z in the formula is hydrogen.

13. Method as claimed in claim 1 wherein Z in the formula is lower alkoxy of from 1 to 6 carbon atoms.

14. Method as claimed in claim 1 wherein Z together with Y in the formula represents an oxo linkage.

15. Method as claimed in claim 1 wherein Z together with Y in the formula represents an alkenyldioxy radical of up to 4 carbon atoms.

16. Method as claimed in claim 1 wherein said compound is 1-ethyl-3-carboxy-1,4-dihydro-7-hydroxy-cyclopenteno-[1,2-h]-quinol-4-one.

17. Method as claimed in claim 1 wherein said compound is 1-allyl-3-carboxy-1,4-dihydro-7-hydroxy-cyclopenteno[1,2-h]-quinol-4-one.

18. Method as claimed in claim 1 wherein said compound is 1-ethyl-7-acetoxy-3-carboxy-1,4-dihydrocyclopenteno[1,2-h]quinol-4-one.

19. Method as claimed in claim 1 wherein said compound is 7-hydroxy-3-ethoxycarbonyl-4-hydroxy-cyclopenteno[1,2-h]-quinoline.

20. Method as claimed in claim 1 wherein said compound is applied to the dosage from 10 to 500 mg./kg. of body weight of said subject.

* * * * *